United States Patent
Mackie et al.

(10) Patent No.: US 10,045,696 B2
(45) Date of Patent: Aug. 14, 2018

(54) TISSUE FLUORESCENCE MONITOR WITH AMBIENT LIGHT REJECTION

(71) Applicant: Wisconsin Alumni Research Foundation, Madison, WI (US)

(72) Inventors: Thomas Mackie, Verona, WI (US); Adam Uselmann, Madison, WI (US); Andreas Velten, Madison, WI (US); Surendra Prajapati, Madison, WI (US); Kevin Eliceiri, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 185 days.

(21) Appl. No.: 13/946,363

(22) Filed: Jul. 19, 2013

(65) Prior Publication Data

US 2015/0025391 A1    Jan. 22, 2015

(51) Int. Cl.
*A61B 5/00* (2006.01)
*G01N 21/64* (2006.01)
*A61B 1/04* (2006.01)

(52) U.S. Cl.
CPC .......... *A61B 5/0071* (2013.01); *A61B 5/0062* (2013.01); *A61B 5/0068* (2013.01); *G01N 21/6428* (2013.01); *A61B 1/043* (2013.01)

(58) Field of Classification Search
CPC .............................. A61B 5/0071; A61B 5/0062
USPC ......................................................... 600/476
See application file for complete search history.

(56) References Cited

U.S. PATENT DOCUMENTS

| | | | | |
|---|---|---|---|---|
| 4,768,513 A | * | 9/1988 | Suzuki | 600/476 |
| 5,120,953 A | * | 6/1992 | Harris | 250/227.2 |
| 6,633,328 B1 | * | 10/2003 | Byrd | A61B 19/52 348/143 |
| 7,045,783 B2 | | 5/2006 | Matveev | |
| 8,169,696 B2 | | 5/2012 | Yazdanfar et al. | |
| 8,498,695 B2 | | 7/2013 | Westwiek et al. | |
| 2004/0082863 A1 | | 4/2004 | McGreevy et al. | |
| 2004/0212808 A1 | * | 10/2004 | Okawa et al. | 356/479 |
| 2004/0215060 A1 | * | 10/2004 | Ueno | A61B 1/00009 600/160 |
| 2006/0004292 A1 | | 1/2006 | Beylin | |
| 2007/0276258 A1 | * | 11/2007 | Crane | 600/476 |
| 2008/0103390 A1 | * | 5/2008 | Contag | A61B 19/52 600/427 |

(Continued)

FOREIGN PATENT DOCUMENTS

WO    2014124537 A1    8/2014

OTHER PUBLICATIONS

Sexton et al., "Plused light imaging for fluorescence guided surgery under normal room lighting", Poster and Summary presented Jun. 10, 2013 at Biophotonics 2013.*

(Continued)

*Primary Examiner* — Christopher Cook
(74) *Attorney, Agent, or Firm* — Boyle Fredrickson, S.C.

(57) ABSTRACT

Fluorescent markers used to identify a tissue may be imaged in a bright environment by synchronizing the imaging process with rapidly switched ambient lighting so that imaging occurs in phase with a switching off of the ambient lighting. In this way, valuable fluorescent imaging may be performed in an environment that appears to be brightly illuminated, for example in the area of a surgical suite.

10 Claims, 5 Drawing Sheets

(56) References Cited

U.S. PATENT DOCUMENTS

| | | | | |
|---|---|---|---|---|
| 2009/0146077 A1* | 6/2009 | Moy | ............... | A61B 1/0638 |
| | | | | 250/458.1 |
| 2009/0146583 A1* | 6/2009 | Bhadri | ............ | A61B 3/0008 |
| | | | | 315/294 |
| 2011/0267493 A1* | 11/2011 | Kubo | ............ | A61B 1/00009 |
| | | | | 348/223.1 |
| 2013/0063565 A1* | 3/2013 | Hara | ............... | G02B 21/008 |
| | | | | 348/46 |
| 2014/0276008 A1 | 9/2014 | Steinbach et al. | | |
| 2015/0109432 A1* | 4/2015 | Dixon | ............ | G01N 21/6456 |
| | | | | 348/79 |

OTHER PUBLICATIONS

Poster Session #2 list at Biophotonics 2013.*
A Review of the Literature on Light Flicker: Ergonomics, Biological Attributes, Potential Health Effects, and Methods in Which Some LED Lighting May Introduce Flicker; IEEE 2010; IEEE Standard P1789; pp. 1-26.
Wallaschek et al.; Autonomous vehicle front lighting systems; Int. J. Vehicle Autonomous Systems, vol. 10, No. 3, 2012; pp. 256-267.
Sexton et al.; Pulsed-light imaging for fluorescence guided surgery under normal room lighting; NIH-PA Author Manuscript; Sep. 1, 2013 Optical Society of America; 38(17); pp. 3249-3252; US.
Lanni et al.; Compact flashlamp-based fluorescence imager for use under ambient-light conditions; 2007 American Institute of Physics; Review of Scientific Instruments 78, 033702 (2007); Full Document; US.
Davis et al.; Pulsed light imaging for wide-field dosimetry of photodynamic therapy in the skin; Optical Methods for Tumor Treatment and Detection: Mechanisms and Techniques in Photodynamic Therapy XXIII, 2014; Proc. of SPIE vol. 8931 89310W-3; Downloaded From: http://proceedings.spiedigitallibrary.org/ on Apr. 7, 2014 Terms of Use: http://spiedl.org/terms; Full Document; US.

* cited by examiner

TISSUE FLUORESCENCE MONITOR WITH AMBIENT LIGHT REJECTION

STATEMENT REGARDING FEDERALLY SPONSORED RESEARCH OR DEVELOPMENT

CROSS REFERENCE TO RELATED APPLICATION

BACKGROUND OF THE INVENTION

The present invention relates to a medical imaging system for detecting faint fluorescence signals and in particular to a fluorescence imaging system usable in brightly lit environments, for example, in a surgical suite.

Fluorescent marker compounds that target cancerous tumors hold promise in allowing rapid identification of ex vitro tissue, for example, as obtained from a biopsy. The fluorescence signal developed by such marker compounds is relatively faint and normally viewed with special fluorescent microscopes that selectively illuminate the tissue with a proper exciting waveform and that include sensitive imaging systems that can isolate and detect the return fluorescence signal. Multiphoton and confocal microscope optics, for example, may be used to isolate the fluorescence signal from specific tissue while image intensifiers such as photomultiplier tubes or the like may be used to amplify the faint signal for detection.

While such fluorescent markers potentially simplify the identification of tumors, the ability of fluorescent markers to guide surgical procedure is limited by the time required to transport tissue samples to a remote location suitable for fluorescence analysis. Alternatively, the samples are imaged in the operating room, often before extraction from the patient. In this scenario, ambient illumination remains active but is dimmed and light filters are typically used and this limits the speed, sensitivity and applicability of the method due to the reduced signal and added background noise. Alternatively the ambient light needs to be switched off periodically during surgery, interrupting the workflow of the entire team.

SUMMARY OF THE INVENTION

The present invention provides a fluorescence imaging system that coordinates with a rapidly switched ambient lighting system, the latter turning on and off at a speed substantially imperceptible to the human eye. The apparently short periods of darkness during the switching process are exploited to perform fluorescence imaging without significant interference from the ambient light. By making fluorescence imaging compatible with bright illumination, the invention allows the fluorescence imaging equipment to be moved into a surgical suite or used in modified form for in vivo examination of tissue.

Specifically, in one embodiment, the invention provides a medical imaging system for monitoring tissue fluorescence. The imaging system provides a fluorescence imager receiving fluorescence data from a patient's tissue and controllable to be switched between an active-state collecting fluorescence data and an inactive-state not collecting fluorescence data. A synchronization circuit synchronizes the fluorescence imager with an area illuminator switching between an on-state and off-state so that the fluorescence imager is switched to the inactive-state when the area illuminator is in the on-state and the fluorescence imager is switched to the active-state when the area illuminator is in the off-state. A frequency of the switching of the area illuminator is above a flicker rate perceptible to a human observer.

It is a feature of at least one embodiment of the invention to permit fluorescence imaging of marker compounds to be performed in a brightly lit environment, for example, within a surgical suite on a separate microscope system or the like, or at the surgery table for direct imaging of the patient tissue to identify tumor margins and/or confirm full surgical resection of the tumor.

The fluorescence imager may be an image intensifier.

It is a feature of at least one embodiment of the invention to provide a system compatible with fluorescence imagers with highly sensitive detectors as may be needed to properly visualize faint fluorescence. The nature of LEDs and the human eye allow for the duty cycle of the illumination to be much smaller than the duty cycle of the capture cycle, allowing the majority of time to be reserved for capture with a minimal loss of capture time.

Alternatively or in addition, the fluorescence imager may include an electronic optical shutter.

It is thus a feature of at least one embodiment of the invention to provide a means of blocking light to imaging elements that may saturate in bright ambient light.

The fluorescence imager may be a mechanically scanning microscope, for example using a galvanometer, and the synchronization circuit may adjust the inactive-state to occur during ends of a scan where a scanning direction reverses. The microscope may be, for example, a dual or multi-photon fluorescence microscope or confocal microscope or the like.

It is thus a feature of at least one embodiment of the invention to provide a fluorescence imaging system usable with conventional fluorescence imaging equipment. By coordinating the illumination period with ends of the scan, where fluorescence data is not acquired, operation of the system may be substantially invisible to the user.

The synchronization circuit may output a synchronization signal receivable by multiple area illuminators indicating a desired timing of an on-state and off-state of the multiple area illuminators.

It is thus a feature of at least one embodiment of the invention to provide a system that may synchronize an arbitrary number of different light sources needed to illuminate an area and that accommodates possible timing limitations of the scanning process of the fluorescence imager.

Alternatively, the synchronization circuit may receive a synchronization signal from at least one area illuminator indicating a timing of an on- and off-state of the area illuminator and the synchronization circuit may control the fluorescence imager to match the timing of the on- and off-state of the area illuminator.

It is thus a feature of at least one embodiment of the invention to provide a system that may work with relatively simple lighting systems, for example those that maintain a global, stable pattern of on- and off-times, for example, synchronized to a power main frequency.

The fluorescence imager may further be switched between the active-state and a second active-state, the second active-state collecting non-fluorescent data from light reflected off the patient's tissue from the area illuminator and further including a compositing circuit generating an image from a combination of fluorescence data and illumination light data.

It is thus a feature of at least one embodiment of the invention to derive additional independent imaging data from the two states of the area such as may be combined with different relative weights.

These particular objects and advantages may apply to only some embodiments falling within the claims and thus do not define the scope of the invention.

DETAILED DESCRIPTION OF THE PREFERRED EMBODIMENT

Figure 1:
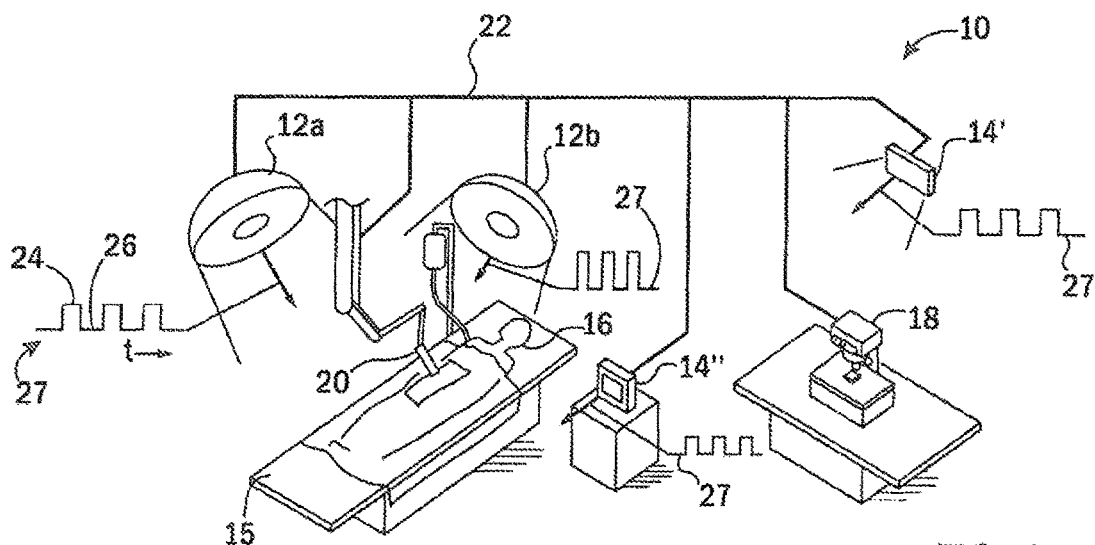
FIG. 1 is a simplified perspective view of a surgical suite in which the present invention may be used showing area illuminators, display lights and a surgical and desktop fluorescence imaging system.

Referring now to FIG. 1, a surgical suite 10 or the like may provide for multiple area illuminators 12a and 12b, for example, positioned to illuminate an operating room table 15 holding a patient 16 for surgery. In addition, the surgical suite 10 may include multiple display lights 14 and other sources of light including, for example, display lights 14 providing for visual signals, for example an illuminated sign display light 14' (e.g. an exit sign) or a computer monitor display light 14" (e.g. an LCD backlight or LED array), presenting data to an attending physician.

The surgical suite 10 may further hold a desktop fluorescence microscope 18 for use contemporaneously with surgery to analyze ex vitro tissue from the patient 16 or a surgical fluorescence surgical imaging system 20, for example, suspended for direct viewing of tissue of the patient in vivo, or at the tip of an endoscope which may provide for microscopic or macroscopic imaging as will be described.

Each of these sources of ambient light (12 and 14) may intercommunicate as indicated by logical communication channel 22 to switch rapidly between an on-state 24 in which light is output and an off-state 26 in which no light is output indicated schematically by illumination signal 27. The logical communication channel 22 will be discussed in detail below and may take a variety of forms not limited to, for example, a wired network.

The illumination signal 27 has a frequency, intensity, and on-state duration so that the output light flashes at a rate substantially above a flicker fusion rate at which the human eye perceives a flashing. The flicker fusion rate is dependent on illumination brightness and other factors but in the present invention will typically be in excess of 24 Hz and preferably above 300 Hz. Generally the intensity of light during the on-state 24 will be such that an average intensity, that is, the intensity of the on-state 24 times the duty cycle of the on-state 24, provides a desired perceived level of illumination comparable to standard illumination levels. Duty cycle refers to the on-state 24 duration divided by the time between successive on-states 24.

Each of the sources of ambient light (12 and 14) may employ a light source that provides substantially white light and which may be rapidly switched between full and no illumination with minimal warm-up time or afterglow to have a rise and fall time constant that is preferably more than five times faster than the frequency of the illumination signal 27. Standard light emitting diodes (LEDs) may be used for this purpose which employs an ultraviolet LED emitter exciting a phosphor or similar material if the phosphor has a short fluorescence lifetime on the order of tens of microseconds. Alternatively, the light emitting diodes may employ a combination of red, green, and blue (and optionally orange) light emitting diodes and no phosphor to simulate white light with no phosphor afterglow.

Figure 2:
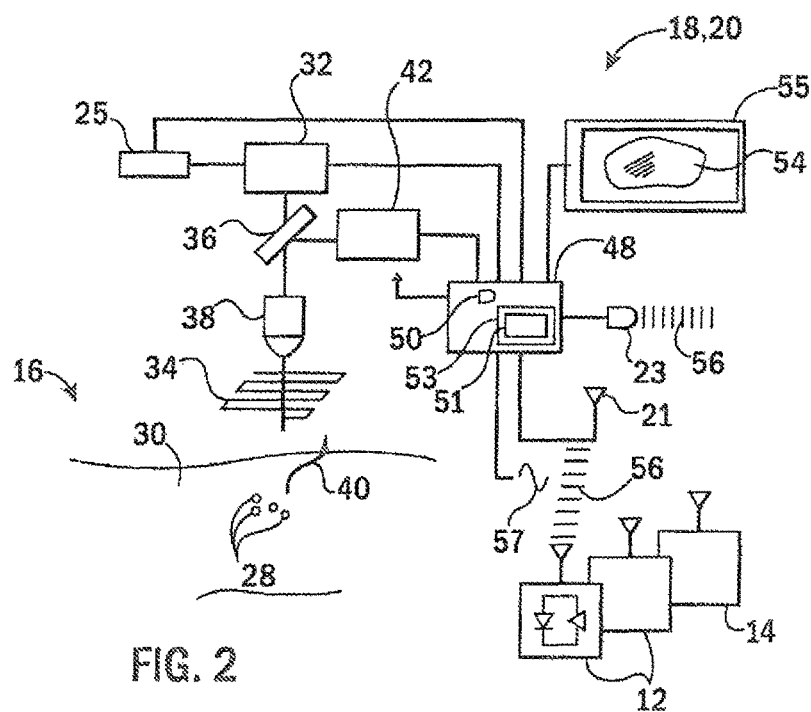
FIG. 2 is a functional block diagram of a fluorescence imaging system of FIG. 1 having a synchronization circuit such as may output a signal to coordinate with area illuminators or Which may receive signals from area illuminators to coordinate fluorescence image acquisition by an optical detection system with illumination dark times.

Referring now to FIG. 2, either or both of the fluorescence imaging microscopes 18 and surgical imaging system 20 may provide for an exciting light source 25, for example, a laser having a frequency appropriate to excite fluorescence in fluorescent marker compounds 28 in tissue 30 of the patient 16. Light source 25 may direct a beam to a galvanometer mirror scanner 32 or similar device which scans the beam from the light source 25 in a raster 34 through the tissue 30. In this regard, the beam may be directed first through a beam splitter 36 then a microscope objective 38. A returning fluorescence 40 may be received by the objective 38 and diverted by the beam splitter 36 to optical detection system 42 as will be described further below, An electronic computer 48 including a processor 50 executing a stored program 51 in memory 53 may output control signals to the light source 25 and the galvanometer mirror scanner 32 to control the same and receive data signals from the optical detection system 42 to provide a fluorescence image 54 on a display 55. As is generally understood in the art, the fluorescence image 54 is generated by mapping signal intensity detected by the optical detection system 42 to a known spatial position of the light beam in the patient tissue according to the raster 34.

The electronic computer 48 may also operate to output a synchronization signal 56 on the communication channel 22 in a variety of means, including by wire conductor or wirelessly as shown as a radio or light signal. The light signal may, for example, be an infrared signal that may be filtered and modulated to be distinguished from ambient light or the ambient light signal itself as will be transmitted by photo element 23. Alternatively, the radio signal may be, for example, a conventional Bluetooth signal or "Wi-Fi" signal, for example, conforming to IEEE 802.11 standards and transmitted by antenna 21. The synchronization signal 56, as will be discussed below, is received by the area illuminators 12 and display lights 14 to coordinate their light output with the operation of the microscope 18.

Alternatively, the electronic computer 48 may operate to receive the synchronization signal 56 on the communication channel 22. Again the medium of communication may be wired or wireless with the wireless signal being a radio signal received by antenna 21 or an infrared or light signal received by photo element 23. The synchronization signal 56 may be transmitted by the area illuminators 12 and or display lights 14. Alternatively, the received synchronization signal 56 may be an external global reference 57, for example, derived from the power line frequency or an external source such as a GPS time signal or the like.

As will be discussed below, in the case where the synchronization signal 56 is transmitted from computer 48, the fluorescence imaging microscope 18 or surgical imaging system 20 will serve to control the switching speed of the area illuminators 12 and display lights 14. In contrast, when the synchronization signal 56 is received by the computer 48, the fluorescence imaging microscope 18 or surgical imaging system 20 will conform its operation to the switching speed of the area illuminators 12 and display lights 14 or to an external global time reference.

Figure 3:
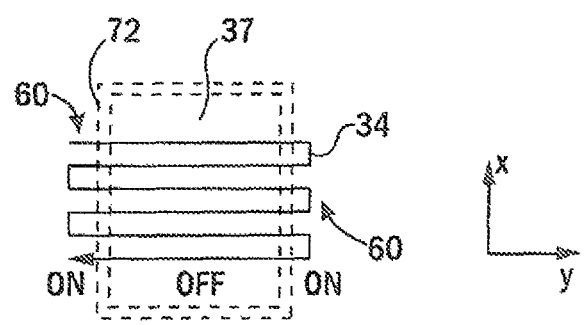
FIG. 3 is a simplified diagram of a raster scan implemented by the fluorescence imager of FIG. 2 showing coordination of the scan with illumination on-and off-times in one embodiment of the invention.
Figure 4:
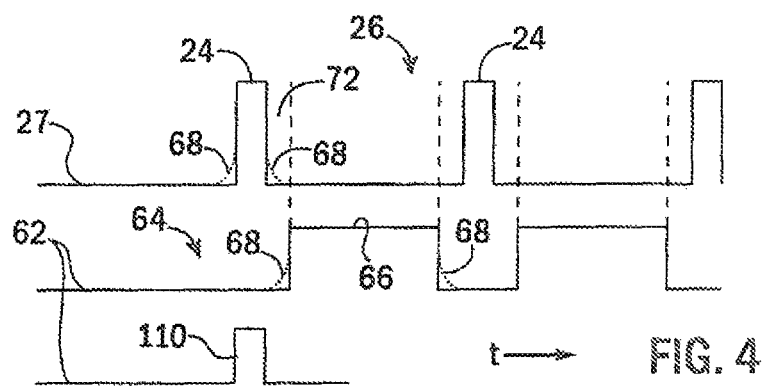
FIG. 4 is a graph showing the on- and off-states of the external light sources and a phase and frequency-aligned gated acquisition of fluorescent data in one embodiment of the present invention.

Referring now also to FIGS. 3 and 4, generally the raster 34 scanned by the fluorescence imaging microscope 18 or surgical imaging system 20 will cover a region of interest 37 in which a fluorescence image 54 will be obtained but will also proceed beyond the region of interest 37 to raster end regions 60 at which a direction of scanning changes and during which acquisition of the fluorescence data giving the intensity of fluorescence 40 is not collected. Cessation of data collection in the raster end region 60 is preferred because the complexity of motion and speed in raster end region 60 may make it difficult to map this data accurately. During the time of the raster scan in the raster end region 60, the computer 48 may deactivate the optical detection system 42 as indicated by inactive-state 64 of the image timing signal 62 controlling the optical detection system 42. Conversely, during the time that the raster scan is covering the region of interest 37, the computer 48 may activate the optical detection system 42 as indicated by active-state 66.

When a CCD device is used, a short dead time between frames of data collection can be implemented for illumination. Alternatively, one could also use a high frame rate CCD or CMOS device and and use every n-th frame for illumination and discard the data or place a shutter in front of the sensor.

The computer 48 operates to synchronize the image-timing signal 62 with the illumination signal 27 so that the two signals have the same frequency and so that they are phased such as to place the active-state 66 of the imager in the off-state 26 of the area illuminators 12 and display lights 14.

Generally, the active-state 66 will be set to be somewhat shorter than the off-state 26 to accommodate the rise and fall time constants of the area illuminators 12 and display lights 14 and of the optical detection system 42. With respect to the former, the time it takes for light to move between the on-state 24 and off-state 26 (or vice versa) may not be immediate, particularly for phosphor LEDs, but subject to a rise and/or fall time 68. Likewise the optical detection system 42 may take some time to switch fully on or fully off as indicated by rise time or fall time 68. Accordingly a time delay period 72 may separate each of the on-state 24 pulses from the active-state 66 in which neither the area illuminators 12 and display lights 14 or the optical detection system 42 are active. The synchronization process will ensure both that the active-state 66 is sufficiently long to accommodate the necessary imaging (e.g. one scan line) and spaced from the pulses of on-state 24, typically by placing some frequency limits on illumination signal 27.

It will be appreciated that the rapid switching of the illumination on and off, which nevertheless provides the visual perception of constant illumination, allows effective operation of the fluorescence microscope 18 without undue light shielding in the dark times of off-state 26. Further because these times can be coordinated with the raster scanning, there is effectively no adverse delay in operation of the microscope 18.

Figure 5:
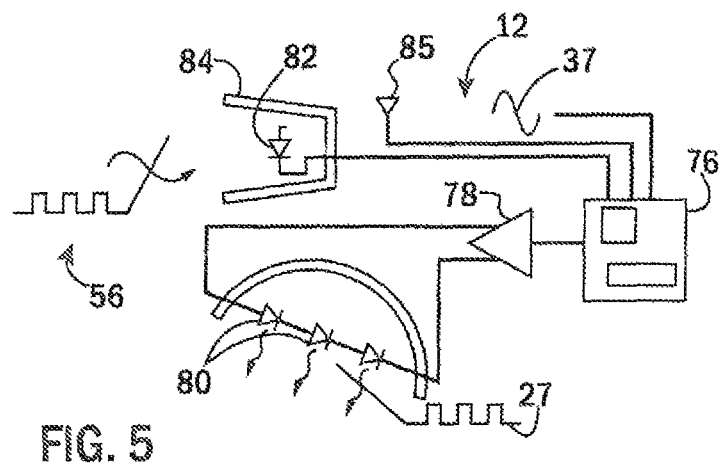
FIG. 5 is a simplified diagram of an area illuminator according to the present invention providing light emitting diodes driven by a driver coordinated with a portion of the synchronization circuit receiving a synchronization signal either from other area illuminators, the fluorescence imager, or line voltage.
Figure 6:
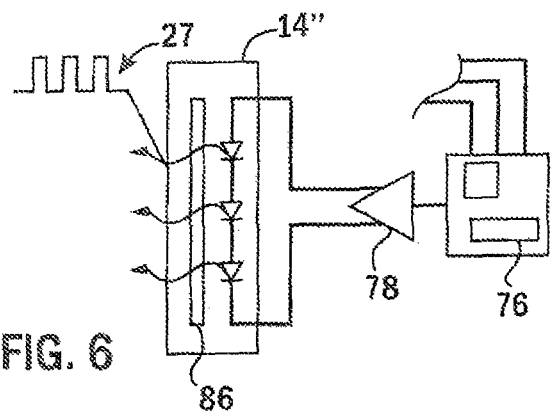
FIG. 6 is a figure similar to that of FIG. 5 showing light emitting diodes used in a display backlight as maybe also coordinated with a synchronization signal.

Referring now to FIGS. 5 and 6, the area illuminators 12 or display lights 14, like the fluorescence imaging microscope 18 and surgical imaging system 20, may either transmit or receive synchronization signals 56. In this regard each of the area illuminators 12 or display lights 14 may include computer systems 76 holding a processor and memory, the latter with a stored program that may implement the synchronization process. The computer system 76 may communicate with an LED driver 78 controlling the illumination of multiple LEDs 80 according to illumination signal 27. For the area illuminator 12, the LEDs 80 may be positioned in a reflector or the like to provide broad area illumination. In the display light 14, the LEDs 80 may be positioned behind an LCD screen 86 or may be active pixels and LED display.

In the case where the computer system 76 is receiving a synchronization signal 56, the computer system 76 may communicate with a photodiode 82 or other photosensor that may receive an illumination signal 27' from other area illuminators 12 or display lights 14. Light sensor 82 may be shielded with a shield 84 to increase the received illumination signal 27' from these other sources with respect to its own emitted illumination signal 27 from diodes 80. In this case the ambient light itself provides the synchronization signal 56 or the light signal may be an infrared signal from an external clock system or another area illuminator 12 or display lights 14 serving as a master. Alternatively, the synchronization signal may be derived from an external global reference 57, for example line voltage, as described above, or a received signal through an antenna 85 from an external global reference, the microscope 18 or surgical imaging system 20, or the like.

In the case with the computer system 76 transmitting the synchronization signal, that transmission may most easily be provided by light output from the LEDs 80 in the form of illumination signal 27; however, other means of synchronization signal output as discussed elsewhere in the application are also contemplated.

It will be appreciated that the present invention employs a synchronization circuit that may be in any of the microscopes 18 and surgical imaging system 20, the area illuminators 12 and the display lights 14 or distributed among those components as implemented, for example, by computers 48 and 76 described above.

Figure 7:
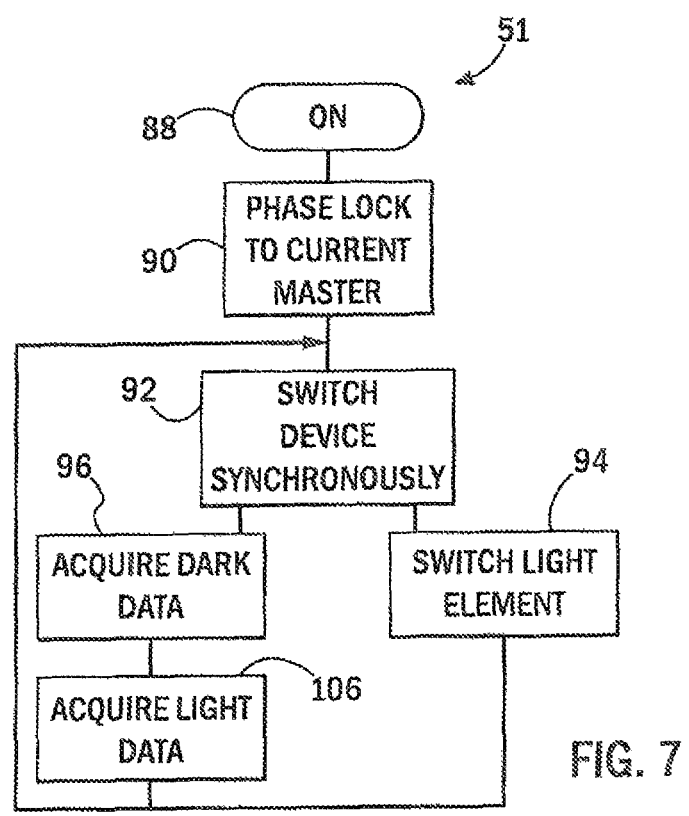
FIG. 7 is a flowchart of the steps implemented by the synchronization circuit.

Referring now to FIG. 7, each of computers 48 and 76, when the respective devices is turned on as indicated by process block 88, may begin a monitoring phase 90 in which any received synchronization signal 56 is analyzed. During this period of time, the microscope 18 and surgical imaging system 20 will not have begun scanning and the area illuminator 12 or display lights 14 will not have turned on their LEDs 80. If no synchronization signal 56 is detected, the device may move to a default mode, for example, of scanning or illumination.

The monitoring phase locks the synchronization signal 56 with an internal clock signal that will be used to operate the associated device either to generate the illumination signal 27 for the area illuminator 12 or display light 14 or to control the speed of the raster scan for the microscope 18 or surgical imaging system 20. The phase locking may use, for example, well-known phase lock loop algorithms which provide a control loop constantly adapting to minor phase variations.

Depending on the device type the internal clock signal may be used to produce the illumination signal 27 used to switch the light element (e.g. LEDs 80) of the area illuminators 12 or sign lights 14 as indicated by process block 94. Alternatively for the microscope 18 or surgical imaging system 20 and as indicated by process blocks 96, internal clock signal (which may provide image timing signal 62) may be used to time the acquisition of data during off-states 26.

When the synchronization signal 56 is the illumination signal 27 from other light devices, it will be understood that as each area illuminator 12 or display light 14 is turned on it synchronizes itself with the other systems in the room so that all are operating in unison.

Figure 8:
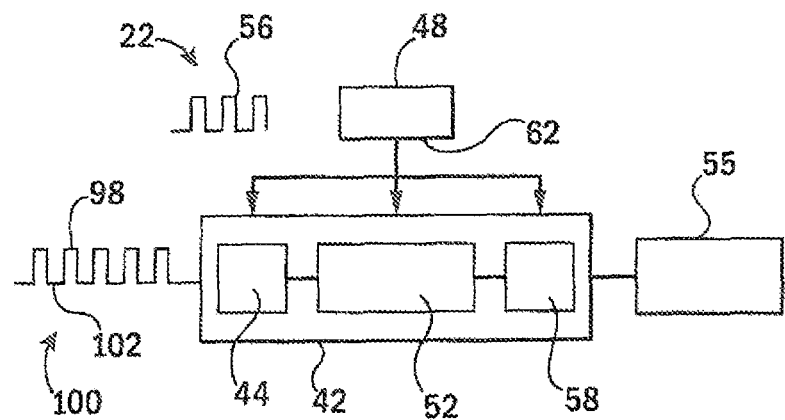
FIG. 8 is a detailed block diagram of the optical detection system of FIG. 2.

Referring now to FIG. 8, a received synchronization signal 56 from a computer 48 may be used to generate image timing signal 62 as described above that may be provided to the optical detection system 42 to switch it between the active-state and inactive-state also described above. The switching process may be implemented by a variety of means including the opening and closing of an electronic shutter 44 (such as a Kerr cell, Pockels cell or high-speed liquid crystal device). The electronic shutter 44 may be oriented to receive a mixed visible light signal 98 and fluorescence signal 102 where the fluorescence signal 102 would normally not be perceptible and a switch to pass only the fluorescence signal 102. Alternatively or in addition, the switching may be implemented by control of an image intensifier 52 positioned after the electronic shutter 44 or used instead of the electronic shutter 44. Switching of the image intensifier 52 may be done, for example, in the case of a photomultiplier tube by switching on and off the electron accelerating voltage. For some types of image intensifiers, use of electronic shutter 44 will prevent saturation during a received light signal 98 providing improved time discrimination. Alternatively or in addition, the switching may be performed by control of the detector 58, for example, of a vidicon tube, charge-coupled device (CCD), avalanche photodiode (APD) array (also considered herein an image intensifier). CMOS detector or the like. The function of the image intensifier 52 and the detector 58 may be combined in a microchannel plate or the like. The surgical imaging system 20 is not necessarily a scanning microscope, but may be, for example, an epifluorescence microscopy, or the like or may be a non scanning or macroscopic system as will be discussed with respect to FIG. 10.

Figure 9:
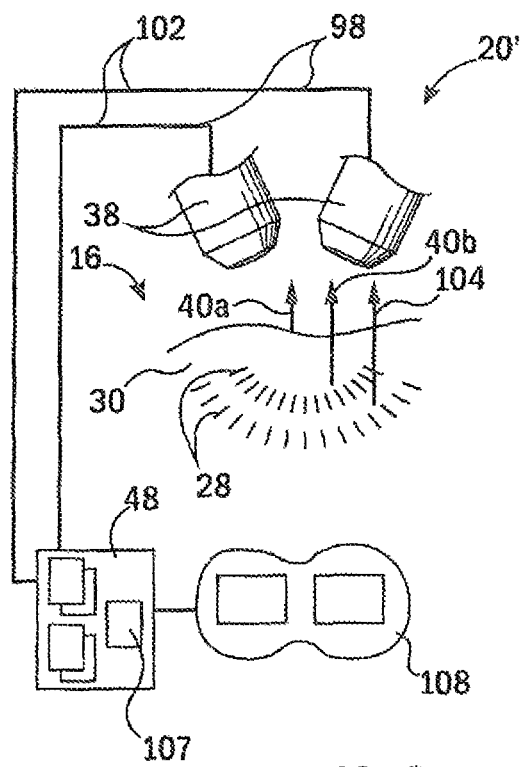
FIG. 9 is a block diagram of a compositing circuit for providing combination fluorescence/visible light images.

In one embodiment shown in FIG. 9, a binocular fluorescence imaging microscope 20' may be provided to collect multiple frequencies of fluorescence 40a and 40b, for example, associated with different markers having different operating depths (generally lower frequency fluorescence may be transmitted further through tissue 30). Referring also to FIGS. 4 and 7, visible light 104 may be collected by the microscope 20 in synchrony with the synchronization signal 56 as indicated by process block 106 by providing unintensified imaging during a second activation state 110 aligned with on-state 24. This visible light 104 may be collected by the detector 58 (shown in FIG. 8) without activation of the image intensifier 52 or using a separate detector 58 for this purpose. In one embodiment, fluorescence signal 102 and visible light signal 98 may be collected for two different angles by multiple objectives 38 of the fluorescence imaging microscope surgical imaging system 20.

A compositor 107 (for example, implemented as a program on computer 48) may receive the two angles of fluorescence signal 102 and visible light signal 98 and may provide a weighting to each of the fluorescence signal 102 and visible light data before combining them into a left and right composite image viewable on binocular display 108. This binocular display 108 provides additional depth information for various fluorescent markers visible in the fluorescence signal 102 referenced to the tissue surface imaged in visible light using visible light signal 98.

While the invention has been described with respect to its value in the surgical suite, it will be appreciated that it allows sensitive imaging to be performed in any place where perceptively continuous ambient lighting is required or desired. Such sensitive imaging systems may include diffuse optical tomography, optical projection tomogaphy, imaging using ballistic photons, fluorescence lifetime imaging, and others.

Figure 10:
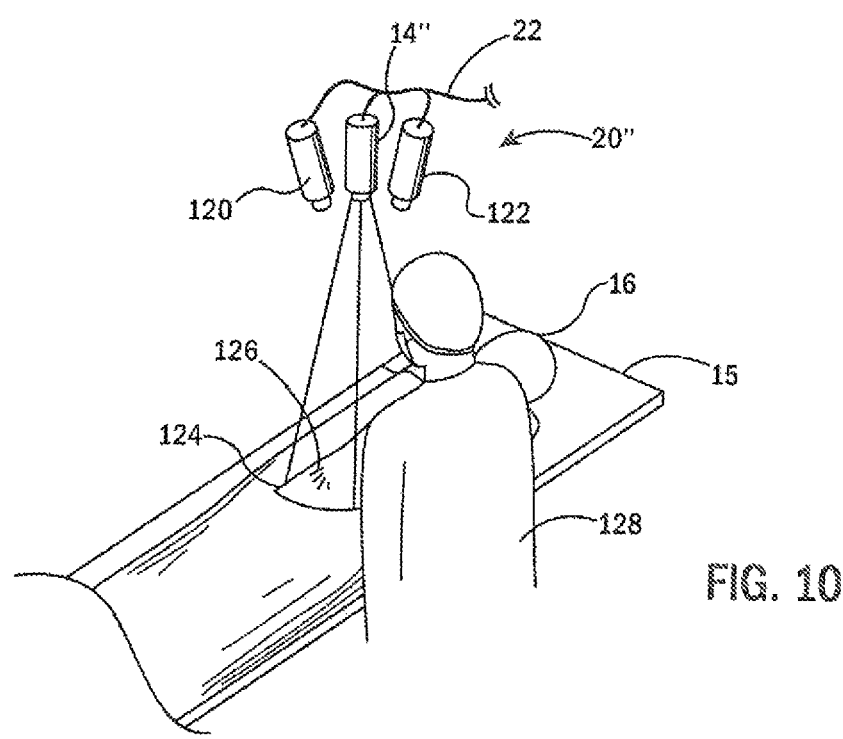
FIG. 10 is a fragmentary perspective view of an alternative embodiment of the invention.

Referring now to FIG. 10, the surgical imaging system 20" need not be a microscope system but may, for example, employ a sensitive macroscopic camera 120 and may be a "single photon" camera coupled with a high-speed narrowband illumination system 122 for exciting fluorescence from tissue of the patient 16 to be detected by the camera 120. The camera 120 and illumination system 122, may for example, be mounted above the operating room table 15 and be directed at a surgical site 124. The display 14" in this case may be in the form of the video projector aligned with the camera 120 so that the text in regions of fluorescence 126 may be augmented by projected images from the projected display 14" registered with the actual tissue. A surgeon 128 may then view the projected image without special equipment, the illumination provided by the display 14" being bright enough for viewing in the switched ambient lighting. In keeping with the above description, the camera 120 is gated to examine fluorescence only during the active state 66 and the projected display 14" is active only during the on-state 24 (see FIG. 4) to which the ambient lighting is synchronized. The illumination provided by illumination system 122 maybe continuously active if desired. As an alternative, the display 14"can be presented to the surgeon 128 via a conventional display screen 14', or by video glasses. The camera 120 does not need sufficient spatial resolution to resolve the fluorescent areas if it is highly sensitive to the fluorescent light. This projected or augmented reality image can be dynamically tuned to provide any combination of the co-registered ambient lit, fluorescent, or other image source.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the synchronization circuit" can be understood to include one or more circuits that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. A medical imaging system for tissue imaging in a surgical suite comprising:
    a communication channel;
    multiple area illuminators switching between an on-state, providing area illumination light, and an off-state, not providing area illumination light, in accordance with a timing signal providing that the multiple area illuminators are in the off-state for a majority of a time between successive initiations of the on-state and received over the communication channel, the area illuminators sized and positioned to illuminate an operating room table during surgery at a level allowing direct viewing by a physician of a patient's tissue during surgery;
    a computer monitor having a source of illumination switching between an on-state providing display illumination and an off-state, not providing display illumination, in accordance with the timing signal providing that the display illumination is in the off-state for a majority of a time between successive initiations of the on-state and received over the communication channel, the computer monitor sized to be positioned with respect the operating room table at the level allowing direct viewing by the physician of the computer monitor during surgery;
    an exciting light source having a frequency adapted to excite fluorescence in the patient's tissue;
    an imager imaging fluorescence from the patient's tissue as stimulated by the exciting light source to produce a fluorescence image; and
    a synchronization circuit communicating with the imager, the computer monitor, and the area illuminators over the communication channel to produce a fluorescence image by synchronizing the imager with switching of the area illuminators and the light source of the computer monitor, between the on-state and the off-state so that the imager is switched to an inactive-state with respect to generating the fluorescence image when the area illuminators and the light source of the computer monitor are in the on-state and the imager is switched to an active-state with respect to generating the fluorescence image when the area illuminators and the light source of the computer monitor are in the off-state and so that the imager is in the active-state for a majority of a capture cycle of one on-state and one off-state;
    wherein a frequency of the switching of the area illuminators is above 24 hertz.

2. The medical imaging system of claim 1 wherein the imager includes an image intensifier.

3. The medical imaging system of claim 1 wherein the synchronization circuit outputs a synchronization signal receivable by multiple area illuminators indicating a desired timing of the on-state and the off-state of the multiple area illuminators.

4. The medical imaging system of claim 1 wherein the synchronization circuit receives a synchronization signal from at least one area illuminator indicating a timing of the on-state and the off-state of the area illuminator and wherein the synchronization circuit controls the imager to match the timing of the on-state and the off-state of the area illuminator.

5. The medical imaging system of claim 1 wherein the imager operating in the inactive-state preserves acquired image frames with respect to an area illumination image and further including a compositing circuit generating an image from a combination of the fluorescence image and the area illumination image.

6. The medical imaging system of claim 1 wherein the light element is at least one light emitting diode.

7. The medical imaging system of claim 1 wherein further including an illuminated sign having a source of illumination switching between an on-state providing sign illumination and an off-state, not providing sign illumination, in accordance with the timing signal providing that the sign illumination is in the off-state for a majority of a time between successive initiations of the on-state and received over the communication channel;
    wherein the synchronization circuit further communicates with the illuminated sign over the communication channel to produce a fluorescence image by synchronizing the imager with switching of the illuminated sign between the on-state and the off-state so that the imager is switched to an inactive-state with respect to generating the fluorescence image when the illuminated sign is in the on-state and the imager is switched to an active-state with respect to generating the fluorescence image when illuminated sign is in the off-state.

8. The medical imaging system of claim 1 wherein the imager further images the patient's tissue as illuminated by the area illuminators when operating in the inactive-state to produce an area illumination image and further including a compositing circuit generating an image from a combination of the fluorescence image and the area illumination image.

9. The medical imaging system of claim 1 further including an area light imager imaging area light reflected by the patient's tissue from the area illumination light and further including a compositing circuit generating an image from a combination of the fluorescence image from the imager and an area light image from the area light imager.

10. The medical imaging system of claim 1 wherein the imager operates at a frame rate to acquire multiple image frames during a capture cycle of one on-state and one off-state during the active-state and inactive-state and wherein image frames acquired during the inactive-state are not used in the fluorescent image.

* * * * *